United States Patent
Rodriguez

(10) Patent No.: US 7,242,986 B2
(45) Date of Patent: Jul. 10, 2007

(54) DEVICE AND METHOD FOR A SELF-ATTACHING SUTURE SLEEVE

(75) Inventor: Luis M. Rodriguez, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 503 days.

(21) Appl. No.: 10/409,433

(22) Filed: Apr. 7, 2003

(65) Prior Publication Data

US 2004/0199233 A1 Oct. 7, 2004

(51) Int. Cl.
*A61N 1/05* (2006.01)

(52) U.S. Cl. ........................ 607/116; 607/132

(58) Field of Classification Search ............... 607/115, 607/116, 119, 126, 149; 606/232; 604/174, 604/175
See application file for complete search history.

(56) References Cited

U.S. PATENT DOCUMENTS

| 5,107,856 A | * | 4/1992 | Kristiansen et al. | 607/126 |
|---|---|---|---|---|
| 5,152,298 A | * | 10/1992 | Kreyenhagen et al. | 607/116 |
| 5,242,431 A | * | 9/1993 | Kristiansen | 604/533 |
| 5,352,198 A | * | 10/1994 | Goldenberg et al. | 604/95.04 |
| 5,397,342 A | | 3/1995 | Heil, Jr. et al. | |
| 5,674,272 A | * | 10/1997 | Bush et al. | 607/122 |
| 5,683,403 A | | 11/1997 | Adams et al. | |
| 6,132,456 A | * | 10/2000 | Sommer et al. | 607/127 |
| 2002/0111663 A1 | * | 8/2002 | Dahl et al. | 607/122 |

* cited by examiner

*Primary Examiner*—Carl Layno
*Assistant Examiner*—Eric D. Bertram
(74) *Attorney, Agent, or Firm*—Schwegman, Lundberg, Woessner & Kluth, P.A.

(57) ABSTRACT

A tubular, suture sleeve to efficiently position and secure an implantable lead thereto without the use of a suture is disclosed. The sleeve comprises first and second ends with first and second inner lumens respectively. The first end is relatively rigid in comparison to the more flexible second end. The circumference of the inner lumen of the first end is larger than a circumference of a lead body to allow the suture sleeve to slide easily along the longitudinal axis of the lead body. The second end is movable between furled and unfurled positions. When unfurled, the inner lumen of the second end is smaller than a circumference of the lead body, thereby allowing the second end to snugly grip the lead body and secure the sleeve at the desired location along the longitudinal axis of the lead body without the use of a suture.

21 Claims, 2 Drawing Sheets

DEVICE AND METHOD FOR A SELF-ATTACHING SUTURE SLEEVE

TECHNICAL FIELD

The present device relates generally to a suture sleeve for an implantable medical device lead and particularly, but not by way of limitation, to such a suture sleeve that is adapted to attach to the lead body of an implantable medical device without the use of sutures.

BACKGROUND

Heart disease is a major health risk in the United States and elsewhere. One well-known treatment approach utilizes an implantable medical device, like a cardiac pacing device (i.e., a pacemaker) or a defibrillator, to manage a patient's heart rate or correct cardiac arrhythmias. An arrhythmia is generally defined as an abnormal cardiac rhythm.

A pacemaker delivers a relatively mild, periodic electrical impulse to epicardial or endocardial tissue as necessary to maintain normal sinus rhythm. In comparison to a pacemaker, an implanted defibrillator applies a much stronger electrical stimulus to the heart to "shock" it into a normal rhythm. The electrical charges for both implanted pacemakers and defibrillators are applied through electrically conductive leads that emanate from the medical device and terminate at an appropriate location on the tissue.

Suture sleeves are used to secure the implanted lead at the implant site. Suture sleeves are generally configured as tubular members, the cavity or lumen of which is adapted to sheathe the electrically conductive lead body of an implantable medical device. A suture sleeve also includes circumferential grooves adapted to receive a suture. The circumferential grooves facilitate wrapping the suture sleeve with a suture to secure the sleeve to the body of a lead and to a patient's body tissue, usually the fascia tissue of the heart. Suture leads are typically formed of soft, implantable elastomer material, such as silicone.

Suture sleeves come in several configurations. Some come from the implantable medical device manufacturer or other distributor with the lead already sheathed by the suture sleeve, thereby eliminating the need to thread or feed the lead through the sleeve during surgery. Other suture sleeves are separate from the lead, and the lead must be fed through the sleeve. Still other suture sleeves include a slit along the longitudinal axis of the sleeve to allow the sleeve to sheathe a lead body by passing the lead through the slit into the cavity or inner lumen of the suture sleeve.

Once the lead body is sheathed within the suture sleeve and properly positioned at the implant site, the suture sleeve is slid down the lead body to a point near the implant site and wrapped with a suture in the circumferential groove. The suture is pulled tight and tied to longitudinally secure the suture sleeve to the lead. The suture sleeve is then sutured to body tissue. Securing a suture sleeve in this manner is important to provide permanent hemostasis and lead stabilization at the implant site.

However, because suture sleeves must be moved along the longitudinal axis of the lead body during the implantation procedure and are constructed of soft, pliable material, problems may occur. For example, because the inner lumen of a typical suture sleeve is generally cylindrical, friction due to contact between the inside of the suture sleeve and the body of the lead may cause the sleeve to stick to the lead and make it difficult or impossible to slide the sleeve along the longitudinal axis of the lead body. On other occasions, if the clinician pulls the suture too tight when securing the sleeve to the lead, the suture can cut through the soft material of the suture sleeve and the insulation surrounding the lead, thereby damaging the lead. When this happens, the lead must be replaced. Unfortunately, damage to the lead is often not detected until after the surgery is complete, thereby requiring additional surgery to correct the problem and ultimately increasing the total cost of the implantation procedure.

Thus, for these and other reasons, there is a need for a suture sleeve that eliminates the risk of cutting through the sleeve when initially securing the sleeve to a lead body.

SUMMARY

According to one aspect of the invention, there is provided a suture sleeve that is adapted to attach to the lead body of an implantable medical device without the use of a suture. The sleeve comprises an elastic, tubular body including first and second ends. The tubular body of the suture sleeve defines an inner lumen. As used herein, the word lumen refers to the canal, duct or cavity defined by the tubular body of the suture sleeve. Also, as used herein, a "clinician" can be a physician, physician assistant (PA), nurse, medical technologist, or any other patient health care provider.

The first end is relatively rigid in comparison to the second end and further comprises at least one circumferential groove adapted to receive a suture. The circumference of the inner lumen at the first end is generally larger than a typical circumference of a lead body. This reduces contact friction between the inner lumen and the lead to allow a clinician to easily slide the sleeve along the longitudinal axis of the lead body. In one embodiment, the first end further comprises three circumferential grooves, each groove adapted to receive a suture.

The second end is movable between furled and unfurled positions. In the furled position, the circumference of the lumen at the second end adjacent the first end is about equal the first end lumen circumference. Therefore, the suture sleeve with the second end in the furled position does not impede the sliding of the sleeve along the longitudinal axis of a lead body. The circumference of the inner lumen at the second end distal the first end is generally smaller than a typical circumference of a lead body and comprises an elastic, tubular structure that when unfurled onto the lead body, secures the suture sleeve to the lead. Therefore, after the clinician properly positions the suture sleeve along the longitudinal axis of a lead body with the second end in the furled position, the second end is unfurled and the smaller circumference of the elastic second end grips the lead body to secure the suture sleeve at the appropriate location along the body of the lead. In this way, the suture sleeve self-attaches to the lead body without the use of a suture, which is the typical way of securing a suture sleeve to a lead.

In a further embodiment, first and second ends include a slit traversing the longitudinal axis of the sleeve, said slit adapted to receive a lead body passed there through and into the lumen. In a preferred embodiment, the first end comprises three circumferential grooves and a lumen circumference greater than the typical circumference of a lead body, and a second end lumen circumference less than the typical circumference of a lead body.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which are shown by way of illustration specific embodiments or examples. These embodiments may be combined, other embodiments may be utilized, and structural and logical changes may be made without departing from the spirit and scope of the present invention. The following detailed description is, therefore, not to be taken in a limiting sense, and the scope of the present invention is defined by the appended claims and their equivalents.

The present device is described with respect to a suture sleeve adapted to be initially secured to a lead of an implantable medical device without the use of sutures.

Figure 1:
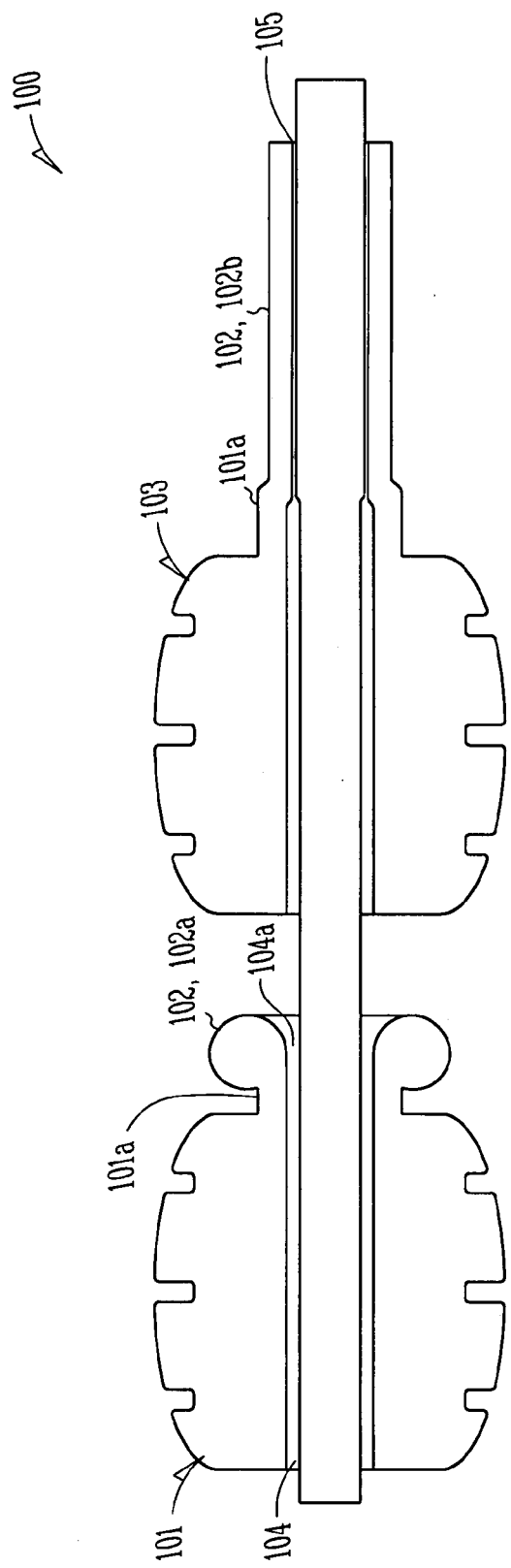
FIG. 1 is an orthogonal view, illustrating generally, among other things, one embodiment of a self-attaching suture sleeve.

FIG. 1 is an orthogonal view, illustrating generally, among other things, one embodiment of a self-attaching suture sleeve 100 comprising an elastic, tubular body including first and second ends. In comparison to the second end 102, the first end 101 of the suture sleeve 100 comprises a relatively rigid tubular structure.

The first end 101 also comprises a least one circumferential groove 103 adapted to receive a suture. However, the primary purpose of the circumferential groove 103 in this embodiment is not to initially secure the sleeve 100 to the lead. It may be used, however, to secure the sleeve 100 to body tissue and, if necessary, assist in securing the sleeve 100 to the lead.

The circumference of the lumen 104 of the first end 101 is adapted to be larger than the circumference of the lumen of the second end 105 and further adapted to be greater than a circumference of a lead body. As further shown in FIG. 1, the circumference of the lumen 104 of the first end 101 is adapted to sheathe a lead in such a way that the sleeve 100 can be longitudinally slid over the lead body with reduced contact, and hence friction, with the lead body. The reduced contact area of the lumen 104 of the first end 101 prevents the sleeve 100 from sticking to the lead body and allows a clinician to easily position the sleeve 100 at the implant site by sliding the sleeve to the desired location.

The second end 102 is movable between furled 102a and unfurled 102b positions. In the furled position 102a, the circumference of the lumen 104a at the termination 110a of the first end 101 is about equal the circumference of the lumen 104 of the first end 101. In the furled position, the second end 102 does not hamper the sleeve's 100 ability to slide easily over the lead body. In the unfurled position 102b, the circumference of the lumen 105 of the second end 102 is generally less than a circumference of a lead body. Because the second end 102 comprises elastic material, it snugly grips a lead body and initially secures the suture sleeve 100 to the lead body when unfurled 102b. Thereafter, a clinician may secure the sleeve 100 to body tissue using circumferential groove 103 or other means.

Figure 2:
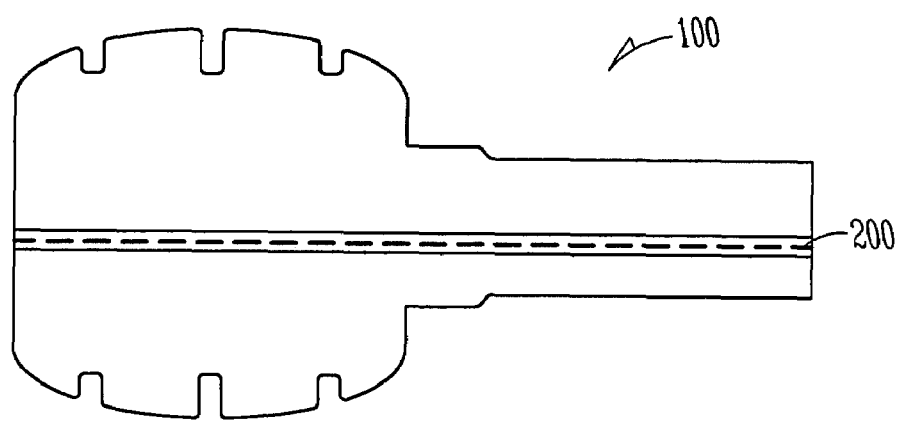
FIG. 2 is an orthogonal view, illustrating generally, among other things, another embodiment of a self-attaching suture sleeve comprising a slit traversing a longitudinal axis of the sleeve.

FIG. 2 is an orthogonal view, illustrating generally, among other things, another embodiment of a self-attaching suture sleeve 100 comprising a slit 200 (exaggerated for illustrative purposes only) traversing a longitudinal axis of the sleeve 100, said slit adapted to receive a lead body passed there through and into first and second end lumens 104, 105. The elastic nature of the suture sleeve 100 biases the slit 200 to a closed position to sheathe and retain a lead body passed through the slit 200. With the slit 200 in the biased, closed position, the tubular body 100 along the slit line is essentially contiguous.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including," "includes" and "in which" are used as the plain-English equivalents of the respective terms "comprising," "comprises" and "wherein."

I claim:

1. A suture sleeve for an implantable lead body comprising:

a tubular body comprising a tubular body first end and a tubular body second end, the tubular body first end including a first end inner lumen and the tubular body second end including a second end inner lumen;

the tubular body first end being rigid in comparison to the tubular body second end and the first end inner lumen being of larger circumference in comparison to the second end inner lumen;

the tubular body first end comprising at least one suture receiving circumferential groove;

the tubular body second end being flexible in comparison to the tubular body first end and the second end inner lumen being of smaller circumference in comparison to the first end inner lumen; and wherein the tubular body further comprises a lead body receiving slit traversing a longitudinal axis of the tubular body.

2. The suture sleeve of claim 1, wherein the circumference of the inner lumen of the tubular body first end is adapted to reduce frictional contact with the lead body.

3. The suture sleeve of claim 2, wherein the circumference of the first end inner lumen is larger than a lead body circumference.

4. A suture sleeve for an implantable lead body comprising:

a tubular body comprising a tubular body first end and a tubular body second end, the tubular body first end including a first end inner lumen and the tubular body second end including a second end inner lumen;

the tubular body first end being rigid in comparison to the tubular body second end and the first end inner lumen being of larger circumference in comparison to the second end inner lumen;

the tubular body first end comprising a plurality of suture receiving circumferential grooves; and the tubular body second end being flexible in comparison to the tubular body first end and the second end inner lumen being of smaller circumference in comparison to the first end inner lumen.

5. The suture sleeve of claim 4, wherein the plurality of suture receiving circumferential grooves comprises three suture receiving circumferential grooves.

6. A suture sleeve for an implantable lead body comprising:

a tubular body comprising a tubular body first end and a tubular body second end, the tubular body first end including a first end inner lumen and the tubular body second end including a second end inner lumen;

the tubular body first end being rigid in comparison to the tubular body second end and the first end inner lumen being of larger circumference in comparison to the second end inner lumen;

the tubular body first end comprising at least one suture receiving circumferential groove;

the tubular body second end being flexible in comparison to the tubular body first end and the second end inner lumen being of smaller circumference in comparison to the first end inner lumen; and wherein the tubular body second end is movable between a furled and an unfurled position.

7. The suture sleeve of claim 6, wherein the tubular body second end is adapted to grip the lead body in the unfurled position.

8. The suture sleeve of claim 7, wherein the circumference of the second end inner lumen in the unfurled position is adapted to increase frictional contact with the lead body.

9. The suture sleeve of claim 8, wherein the circumference of the second end inner lumen in the unfurled position is less than a lead body circumference.

10. The suture sleeve of claim 6, wherein the tubular body second end in the unfurled position secures the suture sleeve to the lead body of an implantable medical device.

11. A method of attaching a suture sleeve comprising two ends and two lumens to the body of a lead of an implantable medical device, comprising the steps of:

sliding the suture sleeve along the longitudinal axis of the lead body until the suture sleeve is at the desired position on the lead body;

unfurling a second end of the suture sleeve to secure the sleeve to the lead body; and securing the suture sleeve to body tissue.

12. The method of claim 11, further comprising sheathing the lead body with the suture sleeve.

13. The method of claim 12, wherein sheathing the lead body includes threading the lead body through a first end of the suture sleeve with the second end being in a furled position.

14. The method of claim 12, wherein sheathing the lead body includes passing the lead body through a longitudinal slit on the suture sleeve into the lumens of the first and second ends, the second end being in a furled position.

15. A suture sleeve attachable to an implantable lead body comprising:

a tubular body extending from a tubular body first end to a tubular body second end, each end including an inner lumen;

wherein the tubular body second end is movable between a furled position including a furled inner lumen and an unfurled position including an unfurled inner lumen, the furled inner lumen having a circumference greater than a circumference of the unfurled inner lumen;

wherein the circumference of the furled inner lumen is about equal to a circumference of the tubular body first end inner lumen; and wherein the tubular body first end comprises a relatively rigid structure in comparison to the tubular body second end.

16. The suture sleeve of claim 15, further comprising at least one suture receiving circumferential groove.

17. The suture sleeve of claim 15, further comprising a lead body receiving slit traversing a longitudinal axis of the tubular body.

18. The suture sleeve of claim 15, wherein the circumference of the unfurled inner lumen is less than a lead body circumference.

19. The suture sleeve of claim 15, wherein the circumference of the furled inner lumen is greater than a lead body circumference.

20. A suture sleeve for an implantable lead body comprising:

a tubular body extending from a tubular body first end to a tubular body second end, each of the tubular body first end and the tubular body second end including an inner lumen;

at least one suture receiving circumferential groove disposed on a portion of the tubular body first end;

wherein the tubular body second end is movable between a furled position including a furled inner lumen and an unfurled position including an unfurled inner lumen; and wherein a circumference of the furled inner lumen is about equal to a circumference of the tubular body first end inner lumen and a circumference of the unfurled inner lumen is less than the circumference of the tubular body first end inner lumen.

21. The suture sleeve of claim 20, wherein the tubular body comprises an elastic material.

* * * * *